(12) United States Patent
Kanner et al.

(10) Patent No.: US 9,102,970 B2
(45) Date of Patent: *Aug. 11, 2015

(54) **PROCESS FOR PRODUCTION OF RECOMBINANT HUMAN GROWTH HORMONE USING GROWTH MEDIA WITH ADDED TRACE ELEMENTS FROM *E. COLI* CELLS**

(71) Applicant: Ferring B.V., Hoofddorp (NL)

(72) Inventors: Dov Kanner, Copenhagen S (DK); Eli Schmell, Copenhagen S (DK)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/276,838

(22) Filed: May 13, 2014

(65) Prior Publication Data

US 2014/0255992 A1 Sep. 11, 2014

Related U.S. Application Data

(63) Continuation of application No. 13/822,210, filed on Mar. 11, 2013, which is a continuation of application No. PCT/IB2011/002348, filed on Sep. 20, 2011, now Pat. No. 8,765,411.

(30) Foreign Application Priority Data

Sep. 21, 2010 (EP) .................................. 10177997

(51) Int. Cl.
*C12P 21/02* (2006.01)
*C12N 1/20* (2006.01)
*A61K 38/27* (2006.01)
*C12P 21/00* (2006.01)
*C07K 14/61* (2006.01)
*C12N 1/38* (2006.01)

(52) U.S. Cl.
CPC ............... *C12P 21/005* (2013.01); *C07K 14/61* (2013.01); *C12N 1/20* (2013.01); *C12N 1/38* (2013.01)

(58) Field of Classification Search
None
See application file for complete search history.

(56) References Cited

U.S. PATENT DOCUMENTS

| | | | |
|---|---|---|---|
| 4,742,004 | A | 5/1988 | Hartman et al. |
| 5,702,921 | A | 12/1997 | Tanaka |
| 5,898,030 | A | 4/1999 | Samaritani |
| 7,541,171 | B2 | 6/2009 | Davis et al. |
| 7,998,732 | B2 | 8/2011 | Chartrain et al. |
| 2003/0032036 | A1 | 2/2003 | Agrawal et al. |
| 2009/0035807 | A1 | 2/2009 | McClellan et al. |
| 2010/0047870 | A1 | 2/2010 | Niphadkar et al. |

FOREIGN PATENT DOCUMENTS

WO  WO2009018307 A3  10/2009

OTHER PUBLICATIONS

International Search Report mailed Feb. 1, 2012 which issued in corresponding International Application No. PCT/IB2011/002348.
Patra et al., Optimization of Inclusion Body Solubilization and Renaturation of Recombinant Human Growth Hormone from *Escherichia coli*.—Prot. Expr. Purif. 18, 182-192, 2000.
ATCC catalogue of Bacteria and Phages, 18th Edition, Rockville, MD, (p. 433, 438, 452), 1992.

*Primary Examiner* — Elly-Gerald Stoica
(74) *Attorney, Agent, or Firm* — Fish & Richardson P.C.

(57) ABSTRACT

The subject invention provides an improved process for the production of human growth hormone.

28 Claims, No Drawings

PROCESS FOR PRODUCTION OF RECOMBINANT HUMAN GROWTH HORMONE USING GROWTH MEDIA WITH ADDED TRACE ELEMENTS FROM E. COLI CELLS

CROSS REFERENCE TO PRIOR APPLICATIONS

This is a Continuation of U.S. application Ser. No. 13/822,210 filed on Mar. 11, 2013 (issued on Jul. 1, 2014 as U.S. Pat. No. 8,765,411) which is a U.S. National Phase application under 35 U.S.C. §371 of International Patent Application No. PCT/IB2011/002348, filed Sep. 20, 2011, and claims the priority of European Patent Application No. 10177997.3, filed Sep. 21, 2010 all of which are incorporated by reference herein in their entirety. The International Application published in English on Mar. 29, 2012 as WO 2012/038822 A1 under PCT Article 21(2).

FIELD OF THE INVENTION

The subject invention relates to the field of recombinant human growth hormone (hGH) production.

BACKGROUND

Human growth hormone (hGH), also known as somatropin (INN) or somatotropin, is a protein hormone produced and secreted by the somatotropic cells of the anterior pituitary. Human growth hormone plays a key role in somatic growth in childhood and in metabolism in adulthood through its effects on the metabolism of proteins, carbohydrates and lipids. Human growth hormone is a single polypeptide chain of 191 amino acids having two disulfide bonds, one between Cys-53 and Cys-165, forming a large loop in the molecule, and the other between Cys-182 and Cys-189, forming a small loop near the C-terminus.

Recombinant DNA technology has permitted the production of an unlimited supply of hGH in a number of different systems. One such system is bacteria, for example E. coli. Although such a process is well established and widely used, as any process of technology at all times, also the latter can still be improved upon.

When recombinant hGH is expressed in E. coli cells as inclusion bodies, the inclusion bodies are typically dissolved in the presence of reducing agents and/or chaotropic agents thereby fully renaturing the hGH and facilitating proper folding of the hGH into its bioactive form and mitigating aggregate formation.

SUMMARY OF THE INVENTION

The subject invention now provides for a significant reduction in aggregate formation during hGH production without the need for reducing agents and/or chaotropic agents.

In this regard, the subject invention provides a process for the production of human growth hormone comprising:
(i) fermenting human growth hormone (hGH) producing E. coli cells;
(ii) recovering inclusion bodies from the E. coli cells and dissolving the recovered inclusion bodies at an alkaline pH to provide dissolved hGH;
(iii) optionally lyophilizing dissolved hGH;
characterized in that the fermentation is carried out in a culture medium comprising manganese, zinc, cobalt, molybdenum, calcium, copper, and boron as trace elements.

The subject invention further provides a method for reducing the amount of human growth hormone polymeric forms formed during a process for the production of human growth hormone comprising:
(i) fermenting human growth hormone (hGH) producing E. coli cells;
(ii) recovering inclusion bodies from the E. coli cells and dissolving the recovered inclusion bodies at an alkaline pH to provide dissolved hGH;
(iii) optionally lyophilizing dissolved hGH;
characterized in that the fermentation is carried out in a culture medium comprising manganese, zinc, cobalt, molybdenum, calcium, copper, and boron as trace elements.

DETAILED DESCRIPTION OF THE INVENTION

The process for the production of human growth hormone of the subject invention comprises the steps of:
(i) fermenting human growth hormone (hGH) producing E. coli cells;
(ii) recovering inclusion bodies from the E. coli cells and dissolving the recovered inclusion bodies at an alkaline pH to provide dissolved hGH;
(iii) optionally lyophilizing dissolved hGH;
characterized in that the fermentation is carried out in a culture medium comprising manganese, zinc, cobalt, molybdenum, calcium, copper, and boron as trace elements.

The method for reducing the amount of human growth hormone polymeric forms formed during a process for the production of human growth hormone of the subject invention comprises the steps of
(i) fermenting human growth hormone (hGH) producing E. coli cells;
(ii) recovering inclusion bodies from the E. coli cells and dissolving the recovered inclusion bodies at an alkaline pH to provide dissolved hGH;
(iii) optionally lyophilizing dissolved hGH;
characterized in that the fermentation is carried out in a culture medium comprising manganese, zinc, cobalt, molybdenum, calcium, copper, and boron as trace elements.

"Human growth hormone" and "hGH" as used herein interchangeably, should be understood to encompass recombinant human growth hormone having 191 amino acids or Met-hGH having 192 amino acids (i.e. hGH with one additional methionine at the N-terminus).

An "hGH polymeric form" as used herein should be understood to encompass any form of hGH which is not hGH having 191 amino acids or 192 amino acids (hGH with one additional methionine at the N-terminus) such as, but not limited to, dimers and oligomers of hGH.

"Culture medium" as used herein should be understood to encompass fermentor medium and/or production medium.

The trace elements in the culture medium can be provided in conventional manner, for example by making use of commercially available salts of the trace elements, including acids and bases, and hydrates thereof. They may be introduced into the culture medium in the form of solid salts or in the form of aqueous solutions comprising one or more of the salts. In one embodiment, they are added in the form of a trace elements solution comprising each of the trace elements at a predetermined concentration. The trace elements solution may further contain an acid or base to adjust the pH and, e.g., maintain the trace elements in solution.

Manganese as a trace element may be provided using, e.g., manganese sulfate monohydrate ($MnSO_4 \cdot H_2O$). Zinc as a trace element may be provided by using, e.g., zinc sulfate heptahydrate ($ZnSO_4 \cdot 7H_2O$). Cobalt as a trace element may be provided by using, e.g., cobalt chloride hexahydrate (CoCl$_2$.6H$_2$O). Molybdenum as a trace element may be provided using, e.g., sodium molybdate dihydrate (NaMoO$_4$.2H$_2$O). Calcium as a trace element may be provided using, e.g., calcium chloride dihydrate (CaCl$_2$.2H$_2$O). Copper as a trace element may be provided using, e.g., copper sulfate pentahydrate (CoSO$_4$.5H$_2$O). Boron as a trace element may be provided using, e.g., boric acid (H$_3$BO$_3$). Iron as trace element may also be provided.

The trace elements are present in the culture medium in the following concentration ranges (based on the total volume of the culture medium) ("range") and in one embodiment are present at the indicated particular concentrations ("embodiment"):

| Trace element | Range (μM) | Embodiment (μM) |
|---|---|---|
| Manganese | 4.4-5.4 | 4.9 |
| Zinc | 7.2-8.8 | 8.0 |
| Cobalt | 6.3-7.7 | 7.0 |
| Molybdenum | 6.2-7.6 | 6.9 |
| Calcium | 15.2-18.6 | 16.9 |
| Copper | 5.5-6.7 | 6.1 |
| Boron | 6.0-7.4 | 6.7 |

In one embodiment, the trace elements are used in a trace elements solution which is added to the culture medium. In this embodiment, the trace elements solution is preferably a concentrated aqueous solution containing the trace elements at a concentration which, when used in the culture medium, achieves the above-mentioned concentration ranges.

In one embodiment, the trace elements solution is added to the culture medium at a proportion of from 0.1 to 10 ml/L, based on the total volume of the culture medium, or from 0.2 to 5 ml/L, or from 0.5 to 1 ml/L, or at about 0.8 ml/L.

When the trace elements solution is added to the culture medium at about 0.8 ml/L, it may comprise 1 g/L manganese sulfate monohydrate. It may also comprise 2.8 g/L zinc sulfate heptahydrate. It may also comprise 2 g/L cobalt chloride hexahydrate. It may also comprise 2 g/L sodium molybdate dihydrate. It may also comprise 3 g/L calcium chloride dihydrate. It may also comprise 1.85 g/L copper sulfate pentahydrate. It may also comprise 0.5 g/L boric acid. In one embodiment, the trace elements solution comprises each of the above-mentioned concentrations of the trace elements.

When the fermentation stage is carried out in more than one step, e.g., when preparing a seed culture in a seed fermentor and advancing that seed culture to a production fermentor, the trace elements in accordance with the subject invention are used in at least one step, or more than one step, or in all fermentation steps.

"Alkaline pH" as used herein should be understood to encompass a pH ranging from 10 to 12.5. In one aspect, the alkaline pH is about 12.

It is further envisaged that step (ii), i.e. recovering inclusion bodies and dissolving the recovered inclusion bodies at alkaline pH, does not involve the use of reducing agents and chaotropic agents.

"Reducing agent" as used herein should be understood to encompass an agent capable of reducing protein Cys-Cys bonds. Non-limiting examples of reducing agents are dithiothreitol (DTT), beta-mercaptoethanol, cystein and glutathione.

"Chaotropic agent" as used herein should be understood to encompass an agent that disrupts the three-dimensional structure in macromolecules such as proteins and denatures them.

Non-limiting examples of chaotropic agents are urea, guanidine, thiourea, and lithium perchlorate.

Step (iii) of the process of the subject invention is an optional step which can be carried out in case it is desired to produce the hGH in solid form. In one embodiment, step (iii) comprises a sub-step of purifying the dissolved hGH prior to lyophilization. Likewise, the sub-step of purification can be added to step (ii) in case no lyophilization is carried out.

EXAMPLES

The invention is further described in the following examples, which are not in any way intended to limit the scope of the invention as claimed.

Example 1

Process for the Production of hGH

Manufacturing of hGH consists of methods well known in the art including fermentation and harvesting of hGH producing *E. coli* cells, recovery and dissolution of inclusion bodies and hGH purification and lyophilization.

Fermentation Process

The hGH fermentation process consists of three steps carried out successively in a shaker flask, a seed fermentor and a production fermentor. Fermentation parameters, temperature, agitation, aeration, pressure, pH and oxygen, are fully controlled by a control system which also controls glucose and ammonia consumption.

Inoculum

~1 ml *E. coli* expressing hGH (ATCC No. 39384) was inoculated into a flask containing 200 ml growth medium (20 g/L casein hydrolysate, 10 g/L yeast extract, 5 g/L NaCl and 100 mg/L ampicillin sodium salt). The flask was incubated for ~6 hours on a rotary shaker at ~30° C. at ~250 rpm. At the end of this time, the culture had an optical density at 660 nm (OD) of ~4. A calculated amount of seed culture was inoculated into the seed fermentor.

Seed Fermentor

The seed fermentor medium contained:

| | |
|---|---|
| Casein hydrolysate | 20 g/L |
| Yeast extract | 10 g/L |
| K$_2$HPO$_4$ | 2.5 g/L |
| NaCl | 5 g/L |
| MgSO$_4$•7H$_2$O | 1 g/L |
| Antifoam (PPG) | 0.4 ml/L |
| Glucose | ~50 g/L |
| and optionally: | |
| Trace elements solution | 0.83 mL/L |

1 L trace elements solution consisted of:

| | |
|---|---|
| MnSO$_4$•H$_2$O | 1 g/L |
| ZnSO$_4$ 7H$_2$O | 2.78 g/L |
| CoCl$_2$ 6H$_2$O | 2 g/L |
| Na$_2$MoO$_4$ 2H$_2$O | 2 g/L |
| CaCl$_2$ 2H$_2$O | 3 g/L |

-continued

| | |
|---|---|
| CuSO₄ 5H₂O | 1.85 g/L |
| H₃BO₃ | 0.5 g/L |
| 32% HCl | 100 mL |

The seed fermentor (150 L) was inoculated with seed culture and fermentation proceeded at approximately 30° C., pH 7. Levels of dissolved oxygen were maintained using methods well known to those skilled in the art and when culture OD was above 12, the seed fermentor contents, ~120 L, were transferred into the 1500 L production fermentor.

Production Fermentor

The production medium contained:

| | |
|---|---|
| Casein hydrolysate | 20 g/L |
| Yeast extract | 10 g/L |
| K₂HPO₄ | 2.5 g/L |
| NaCl | 5 g/L |
| MgSO₄•7H₂O | 1 g/L |
| Antifoam (PPG) | 0.4 ml/L |
| Glucose | ~13 g/L |
| and optionally: | |
| Trace elements solution | 0.83 mL/L |

50% glucose solution was added during the production phase. Fermentor temperature was approximately 30° C., pH was maintained at approximately 7 with ammonia, and dissolved oxygen levels were maintained using methods well known to those skilled in the art. At OD 13-16, production of hGH was induced by raising the fermentation temperature from about 30° C. to approximately 42° C. and fermentation proceeded for the next ~2 hours.

Harvest

Bacterial cells containing hGH were harvested by hollow fiber microfiltration. The fermentation broth, ~1200 L, was concentrated and dialyzed against purified water (PuW). The slurry was stored at −10° C. to −30° C.

Recovery and Purification of hGH

Harvest cell slurry was disrupted and washed in PuW resulting in inclusion bodies comprising hGH. The inclusion bodies were dissolved by raising the pH to 12.0±0.1 by adding 1 N NaOH with stirring. hGH was refolded by lowering the pH to 10.5±0.1 and adding 0.5 M borate pH 9.0 to a final concentration of 10 mM borate. No reducing agents nor chaotropic agents were used in the dissolution of the inclusion bodies.

hGH was then purified by methods known in the art including a series of ultrafiltration and chromatography steps. Aminopeptidase, the N-terminal methionine removing enzyme was used during the process to remove the N-terminal methionine from Met-hGH. The purified hGH was finally lyophilized.

Example 2

Comparative Analysis of hGH Produced With and Without Trace Elements

Eleven (11) hGH preparations were produced according to Example 1 with the exception that trace elements (TE) were not added to the seed fermentor medium nor to the production medium.

Twenty-three (23) hGH preparations were produced according to Example 1 where TE were added to the seed fermentor medium and to the production medium.

Table 1 demonstrates that lyophilized preparations resulting from fermentation containing trace elements had a much lower amount of hGH polymeric forms. The amount of hGH polymeric forms is presented as the relative percentage of the total peak area corresponding to all peaks in the analytical size exclusion chromatography (SEC) used in the analysis. The SEC procedure was carried out in accordance with the Somatropin monograph in the European Pharmacopeia 6$^{th}$ edition 2010.

TABLE 1

| Preparation | Trace Element Solution | hGH Polymeric Forms |
|---|---|---|
| I | − | 1.4 |
| II | − | 1.9 |
| III | − | 1.3 |
| IV | − | 1.7 |
| V | − | 2.0 |
| VI | − | 1.8 |
| VII | − | 1.9 |
| VIII | − | 3.0 |
| IX | − | 1.6 |
| X | − | 1.3 |
| XI | − | 1.3 |
| XII | + | 0.7 |
| XIII | + | 0.6 |
| XIV | + | 0.8 |
| XV | + | 0.7 |
| XVI | + | 0.6 |
| XVII | + | 0.9 |
| XVIII | + | 0.8 |
| XIX | + | 0.5 |
| XX | + | 1.0 |
| XXI | + | 0.7 |
| XXII | + | 0.9 |
| XXIII | + | 0.8 |
| XXIV | + | 0.7 |
| XXV | + | 0.8 |
| XXVI | + | 0.9 |
| XXVII | + | 0.8 |
| XXVIII | + | 0.9 |
| XXIX | + | 0.9 |
| XXX | + | 0.7 |
| XXXI | + | 0.7 |
| XXXII | + | 0.8 |
| XXXIII | + | 0.8 |
| XXXIV | + | 0.8 |

The invention claimed is:

1. A process for the production of human growth hormone (hGH) comprising:
   i. fermenting human growth hormone producing *E. coli* cells;
   ii. recovering inclusion bodies from the *E. coli* cells and dissolving the recovered inclusion bodies at an alkaline pH to provide dissolved hGH;
   iii. optionally lyophilizing dissolved hGH;
and wherein the fermentation is carried out in a culture medium comprising manganese, zinc, cobalt, molybdenum, calcium, copper, and boron as trace elements and wherein the culture medium comprises the trace elements in the following concentrations

| | |
|---|---|
| Manganese | 4.4-5.4 μM |
| Zinc | 7.2-8.8 μM |
| Cobalt | 6.3-7.7 μM |
| Molybdenum | 6.2-7.6 μM |

-continued

| | |
|---|---|
| Calcium | 15.2-18.6 μM |
| Copper | 5.5-6.7 μM |
| Boron | 6.0-7.4 μM | based on the total volume of the culture medium.

2. The process according to claim 1, which comprises adding all of the trace elements to the culture medium in the form of a trace elements solution.

3. The process according to claim 2, wherein the trace elements solution comprises 1 g/L manganese sulfate.

4. The process according to claim 2, wherein the trace elements solution comprises 1 g/L manganese sulfate monohydrate, 2.78 g/L-zinc sulfate heptahydrate, 2 g/L-cobalt chloride hexahydrate, 2 g/L-sodium molybdate dihydrate, 3 g/L calcium chloride dihydrate, 1.85 g/L copper sulfate pentahydrate and 0.5 g/L boric acid.

5. The process according to claim 1 wherein the alkaline pH is from about 10 to about 12.5.

6. The process according to claim 5 wherein the alkaline pH is about 12.

7. The process according to claim 1 wherein step (ii) does not use reducing agents and/or chaotropic agents.

8. A method for reducing the amount of human growth hormone polymeric forms formed during a process for the production of human growth hormone (hGH) comprising:
  i. fermenting human growth hormone producing *E. coli* cells;
  ii. recovering inclusion bodies from the *E. coli* cells and dissolving the recovered inclusion bodies at an alkaline pH to provide dissolved hGH;
  iii. lyophilizing dissolved hGH;
carrying out the fermenting step in a culture medium comprising manganese, zinc, cobalt, molybdenum, calcium, copper, and boron as trace elements and wherein the culture medium comprises the trace elements in the following concentrations:

| | |
|---|---|
| Manganese | 4.4-5.4 μM |
| Zinc | 7.2-8.8 μM |
| Cobalt | 6.3-7.7 μM |
| Molybdenum | 6.2-7.6 μM |
| Calcium | 15.2-18.6 μM |
| Copper | 5.5-6.7 μM |
| Boron | 6.0-7.4 μM | based on the total volume of the culture medium and recovering human growth hormone that has a lower level of human growth hormone polymeric forms compared to human growth hormone produced using the same process steps without trace elements.

9. The method according to claim 8, which comprises adding the trace elements to the culture medium in the form of a trace elements solution.

10. The method according to claim 9, wherein the trace elements solution comprises 1 g/L manganese sulfate monohydrate.

11. The method according to claim 9, wherein the trace elements solution comprises the trace elements in the form of 1 g/L manganese sulfate monohydrate, 2.78 g/L zinc sulfate heptahydrate, 2 g/L cobalt chloride hexahydrate, 2 g/L molybdate dihydrate, 3 g/L-calcium chloride dihydrate, 1.85-g/L-copper sulfate pentahydrate and 0.5 g/L boric acid.

12. The method according to claim 8 wherein the alkaline pH is from about 10 to about 12.5.

13. The method according to claim 12 wherein the alkaline pH is about 12.

14. The method according to claim 8 wherein step (ii) does not use reducing agents and/or chaotropic agents.

15. The process according to claim 2, wherein the trace elements solution comprises about 2.8 g/L zinc sulfate heptahydrate.

16. The process according to claim 2 wherein the trace elements solution comprises 2 g/L cobalt chloride hexahydrate.

17. The process according to claim 2 wherein the trace elements solution comprises 2 g/L sodium molybdate dehydrate.

18. The process according to claim 2 wherein the trace elements solution comprises 3 g/L calcium chloride dehydrate.

19. The process according to claim 2 wherein the trace elements solution comprises 1.85 g/L-copper sulfate pentahydrate.

20. The process according to claim 2 wherein the trace elements solution comprises 0.5 g/L boric acid.

21. The method according to claim 9, wherein the trace elements solution comprises about 2.8 g/L zinc sulfate heptahydrate.

22. The method according to claim 9, wherein the trace elements solution comprises 2 g/L cobalt chloride hexahydrate.

23. The method according to claim 9, wherein the trace elements solution comprises 2 g/L sodium molybdate dehydrate.

24. The method according to claim 9, wherein the trace elements solution comprises 3 g/L calcium chloride dehydrate.

25. The method according to claim 9, wherein the trace elements solution comprises 1.85 g/L copper sulfate pentahydrate.

26. The method according to claim 9, wherein the trace elements solution comprises 0.5 g/L boric acid.

27. The process according to claim 2, wherein the trace elements solution comprises at least one member selected from the group consisting of 1 g/L manganese sulfate monohydrate, about 2.8 g/L zinc sulfate heptahydrate, 2 g/L cobalt chloride hexahydrate, 2 g/L sodium molybdate dehydrate, 3 g/L calcium chloride dehydrate, 1.85 g/L copper sulfate pentahydrate and 0.5 g/L boric acid.

28. The method according to claim 9, wherein the trace elements solution comprises at least one member selected from the group consisting of 1 g/L manganese sulfate monohydrate, about 2.8 g/L zinc sulfate heptahydrate, 2 g/L cobalt chloride hexahydrate, 2 g/L sodium molybdate dehydrate, 3 g/L calcium chloride dehydrate, 1.85 g/L copper sulfate pentahydrate and 0.5 g/L boric acid.

* * * * *